(12) United States Patent
Andersen et al.

(10) Patent No.: US 8,449,511 B2
(45) Date of Patent: *May 28, 2013

(54) ACTIVITY OSTOMY BAG

(75) Inventors: Birthe Vestbo Andersen, Marietta, GA (US); Soeren Hansen, Helsingoer (DK)

(73) Assignee: Coloplast A/S, Humlebaek (DK)

( * ) Notice: Subject to any disclaimer, the term of this patent is extended or adjusted under 35 U.S.C. 154(b) by 1144 days.

This patent is subject to a terminal disclaimer.

(21) Appl. No.: 11/662,190

(22) PCT Filed: Sep. 8, 2005

(86) PCT No.: PCT/DK2005/000572
§ 371 (c)(1),
(2), (4) Date: Mar. 8, 2007

(87) PCT Pub. No.: WO2006/026995
PCT Pub. Date: Mar. 16, 2006

(65) Prior Publication Data
US 2008/0097360 A1    Apr. 24, 2008

(30) Foreign Application Priority Data
Sep. 8, 2004    (DK) .................................. 2004 01358

(51) Int. Cl.
*A61F 5/44*    (2006.01)
(52) U.S. Cl.
USPC ........... 604/332; 604/317; 604/318; 604/322; 604/326; 604/331; 604/334; 604/336; 604/337; 604/338; 604/339; 604/340; 604/341; 604/342; 604/343; 604/344; 604/345; 604/348; 604/349; 604/351; 604/353; 604/355; 206/363; 383/100

(58) Field of Classification Search
USPC .................................................. 604/332, 343
See application file for complete search history.

(56) References Cited

U.S. PATENT DOCUMENTS

| 2,520,831 | A | * | 8/1950  | Chincholl  | 604/335 |
| 3,039,464 | A | * | 6/1962  | Galindo    | 604/344 |
| 3,507,282 | A | * | 4/1970  | Burding    | 604/333 |
| 3,655,118 | A | * | 4/1972  | Rinecker   | 383/62  |
| 4,233,977 | A | * | 11/1980 | Mattson    | 604/335 |
| 4,331,148 | A | * | 5/1982  | Steer et al. | 604/333 |
| 4,367,732 | A |   | 1/1983  | Poulsen et al. |       |
| 4,439,191 | A | * | 3/1984  | Hogan      | 604/332 |
| 4,519,797 | A | * | 5/1985  | Hall       | 604/332 |

(Continued)

FOREIGN PATENT DOCUMENTS

| EP | 0 729 733    | 9/1996 |
| EP | 1 378 218 A1 | 1/2004 |

(Continued)

*Primary Examiner* — Tatyana Zalukaeva
*Assistant Examiner* — Ginger T Chapman
(74) *Attorney, Agent, or Firm* — Coloplast Corp., Coloplast A/S; Nick Baumann

(57) ABSTRACT

The ostomy receiving bag comprises a front wall (2) and a rear wall and has a top end and a bottom end. The top end of the rear wall is provided with an inlet to receive a stoma, and one wall is provided with at least one first half of a fixation pair (A), and the same effective wall after closure of the bag, if available, is provided with at least one second half of a fixation pair (B), such that when the first half and the second half of the fixation pair are attached, the volume of the receiving bag is reduced.

20 Claims, 3 Drawing Sheets

U.S. PATENT DOCUMENTS

Figure 1:
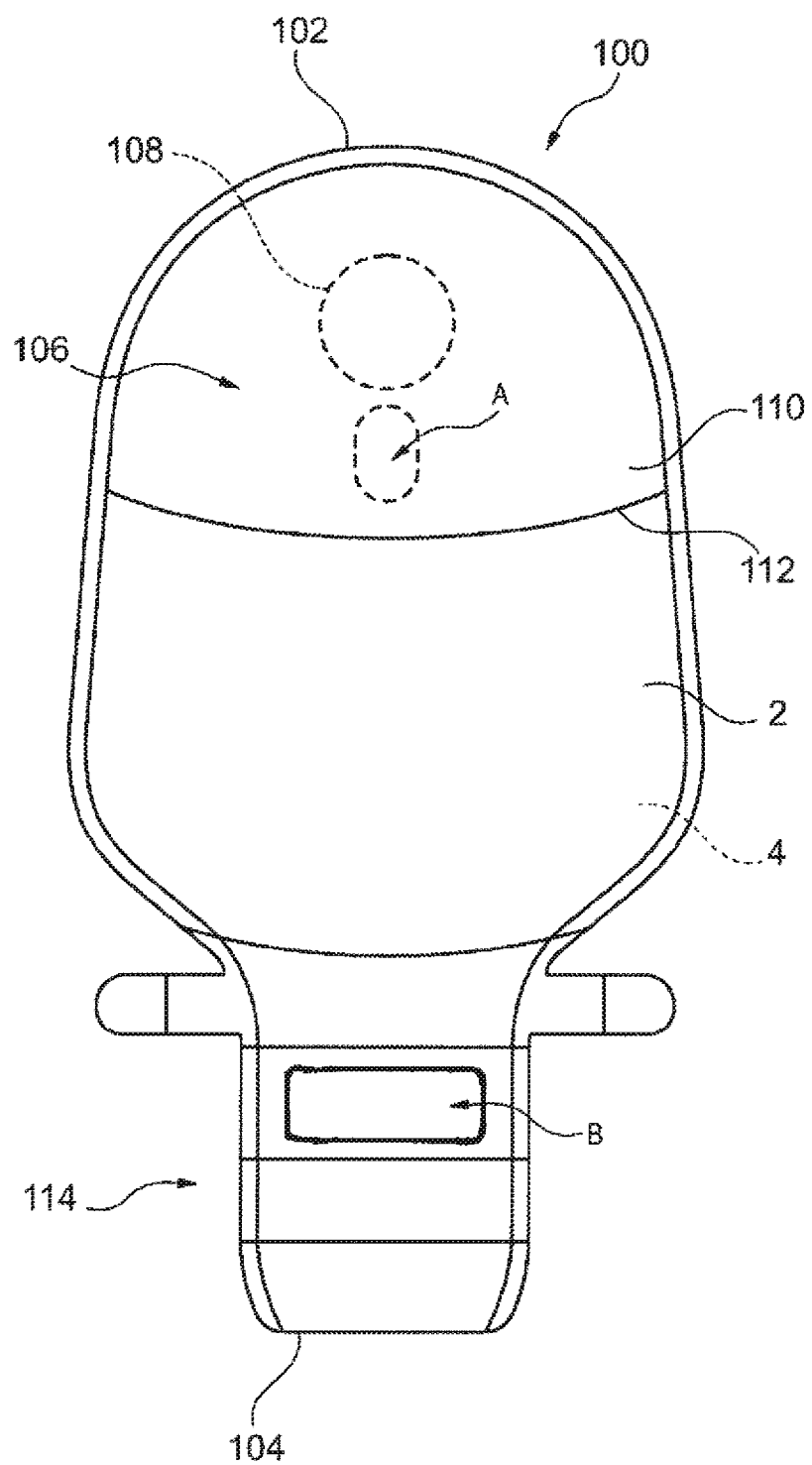

| | | | |
|---|---|---|---|
| 4,543,097 A * | 9/1985 | Van Polen | 604/333 |
| 4,938,747 A * | 7/1990 | Wallace | 604/317 |
| 4,955,879 A | 9/1990 | Mervine | |
| 5,051,259 A | 9/1991 | Olsen et al. | |
| 5,248,308 A * | 9/1993 | von Emster | 604/337 |
| 5,279,603 A | 1/1994 | Everett | |
| 5,607,412 A * | 3/1997 | Brown | 604/332 |
| 5,667,502 A | 9/1997 | Holtermann | |
| 5,714,225 A | 2/1998 | Hansen et al. | |
| 5,800,415 A | 9/1998 | Olsen | |
| 5,843,054 A * | 12/1998 | Honig | 604/345 |
| 6,336,918 B1 * | 1/2002 | Olsen et al. | 604/332 |
| 6,780,172 B2 * | 8/2004 | Olsen et al. | 604/332 |
| D533,273 S * | 12/2006 | Witt | D24/128 |
| D611,595 S * | 3/2010 | Rago | D24/118 |
| 7,691,091 B1 * | 4/2010 | Baggett | 604/317 |
| D624,644 S * | 9/2010 | Rago | D24/118 |
| 2004/0171999 A1* | 9/2004 | Andersen et al. | 604/332 |
| 2006/0111682 A1* | 5/2006 | Schena et al. | 604/334 |

FOREIGN PATENT DOCUMENTS

| | | |
|---|---|---|
| GB | 1316235 | 5/1973 |
| WO | WO 93/18725 | 9/1993 |
| WO | WO 94/18919 | 9/1994 |
| WO | WO 02/102289 | 12/2002 |
| WO | WO 02/102289 A1 * | 12/2002 |

* cited by examiner

ACTIVITY OSTOMY BAG

This is a national stage of PCT/DK05/000572 filed Sep. 8, 2005 and published in English.

FIELD OF THE INVENTION

The present invention relates to a collecting bag to be secured to the abdomen of a patient or to a body side ostomy member for collecting fluids or excretions.

BACKGROUND

The present invention relates to a collecting bag to be secured to the abdomen of a patient or to a body side ostomy member for collecting fluids or excretions emerging from an abdominal stoma.

In connection with surgery for a number of diseases in the gastro-intestinal or urinary tract a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is attached to the base plate. In case of a two-piece appliance, the adhesive barrier member forms part of a body side member and a receiving member or bag is attached releasably to the body side ostomy member for receiving exudates from the stoma.

When using one-piece appliances, the whole appliance, including the adhesive skin barrier securing the appliance to the skin is normally removed and replaced by a fresh appliance. When using two-piece appliances, the body side ostomy member is left in place up to several days, and only the receiving member or bag attached to the body side member is replaced. The attachment means for attaching an ostomy receiving bag may be a system known per se comprising matching coupling rings or matching flanges and adhesive surfaces engaging with and sealing against a flange area of the body side member.

Ostomy receiving bags are available in various sizes for taking into account the different need for collecting capacity of the users, both the difference between different users and also for the individual user according to actual situation and diet. The different sizes may also allow the user to use a small bag or cap for discretion when e.g. when going out or attending public meetings.

However, as the secretion of exudates from the stoma cannot be regulated at will, situations often occur where the actual size of a more discreet collecting bag is not sufficient which may cause severe embarrassment for the user.

Thus, there is a need for a very discreet collecting bag which also offers a solution to an acute demand for a larger capacity of the collecting device.

SUMMARY

The present invention discloses a system to fold an ostomy bag, thereby reducing volume, and maintaining such folded position by fastening means, a fixation pair.

DETAILED DISCLOSURE

Thus, the present invention relates to an ostomy receiving bag 100 (See FIG. 1) comprising a front wall 2 and a rear wall 4 and having a top end 102 and a bottom end 104, wherein
  the top end portion 106 of the rear wall 4 is provided with an inlet 108;
  one wall 2, 4 is provided with at least one first half of a fixation pair A or B; and
  the same effective wall 2 or 4 after closure of the bag 100, if available, is provided with at least one second half of a fixation pair (B or A)
such that when the first half and the second half of the fixation pair A, B are attached, the volume of the receiving bag 100 is reduced. This system offers the users the possibility for extra discretion by reducing the volume of an empty (or nearly empty) pouch (bag 100). Still, the bag 100 is readily expandable when needed. Using this system, it is secured that the folded bag 100 does not tend to fall down during use. A cover sheet 110 is attached to the front wall 2 and includes opening 112. The bottom end 104 provides an outlet tail 114 extending away from the front and rear walls.

Thus, one confirmation of the invention relates to the ostomy receiving bag wherein the bottom end of the receiving bag is folded back and the at least two fixation pairs are attached. This confirmation is preferred when the product is delivered to the customer, and if the customer has just emptied the bag.

The ostomy receiving bag according to the invention may be adapted for use together with an ostomy body side member (2-piece appliance) wherein the receiving bag is provided with coupling means for releasable securing to matching coupling means placed on the ostomy body side member and wherein the inlet opening is adapted for alignment with a hole of the ostomy body side member for receiving a stoma.

The ostomy receiving bag according to the invention may, as an alternative, be adapted for use directly (1-piece appliance) in which case the bag is provided with an adhesive wafer for securing the receiving bag to the user's skin, said bag and wafer having an inlet opening for receiving a stoma.

The receiving bag itself typically comprising front and rear walls sealed together along the rim and provided with an inlet opening may be made in analogy with and from materials conventionally used for the preparation of ostomy appliances.

An ostomy body side member for use together with an ostomy receiving bag according to the invention may be produced from standard materials normally used for preparation of disposable ostomy and wound and incontinence devices. Thus, the adhesive wafer for a body side member or of a 1-piece ostomy appliance bag according to the invention may be made from a medical grade barrier adhesives known in the such as the formulation being disclosed, for example in U.S. Pat. No. 4,367,732, 5,051,259 or 5,714,225. For a 2-piece ostomy appliance according to the invention the body side member and the receiving bag are provided with matching coupling means.

Typical for such production, the ostomy receiving bag according to the invention are manufactured so that the front and rear wall are sealed together along the rim thereof. The coupling means for use in connection with the present invention may be any suitable coupling means known per se for coupling of ostomy base plates to ostomy collecting bags, e.g. a mechanical coupling such as matching coupling rings such as the coupling rings disclosed in WO 93/18725 or WO 94/18919 or matching flanges for adhesive connection of the type disclosed in No. 15 U.S. Pat. No. 5,800,415.

Apart from dividing ostomy bags into one- and two-piece bags, both of these exist as so-called "open" and "closed" bags. A closed bag in the present invention would take the form of an ostomy receiving bag comprising a front and a rear wall and having a top end and a bottom end, wherein the top end of the rear wall is provided with an inlet;
one wall is provided with at least one first half of a fixation pair; and
the same wall is provided with at least one second half of a fixation pair such that when the first half and the second half of the fixation pair are attached, the volume of the receiving bag is reduced.

However, in one embodiment the invention relates to an open bag. An open ostomy bag comprises a closable outlet in the bottom end of the receiving bag, whereby excess semi-liquid material can be drained without removing the bag from the user.

Consequently, in one embodiment of the invention, when the open bag is in it fully unfolded configuration at least one second half of the fixation pair is placed on the opposite wall as at least one of the first half of the fixation pair, but the closure of the open bag results in the two halves of the fixation pair to be on the same side of the ostomy bag.

Many kinds of fixation pairs exist, and are known to the skilled person. In one embodiment referring to FIG. 1 the fixation pair A, B is hook-hook. In another embodiment the fixation pair A, B is hook-loop provided as a hook-loop fixation pair sold under the trademark VELCRO. In yet another embodiment the fixation pair A, B is non-tacky adhesive surfaces. In yet another embodiment the fixation pair A, B is press stud. In yet another embodiment the fixation pair A, B is snap fastener. In yet another embodiment the fixation pair A, B is a popper. In yet another embodiment the fixation pair A, B is glue. In yet another embodiment the fixation pair A, B is press sensitive adhesive (PSA). In yet another embodiment the fixation pair A, B is tape. In yet another embodiment the fixation pair A, B is snap lock. In yet another embodiment the fixation pair A, B is a button combination. In yet another embodiment the fixation pair A, B is clips. In yet another embodiment the fixation pair A, B is a zipper. In yet another embodiment the fixation pair is string A, B. In yet another embodiment the fixation pair A, B is a microbutton combination. In yet another embodiment the fixation pair A, B is an interlocking folding. In yet another embodiment the fixation pair A, B is a magnet combination.

In one particularly preferred embodiment of the invention on the same wall as the fixation pair the receiving bag further comprises at least a stretch of a cover of a sheet material covering the half of the fixation pair closest to the top of the receiving bag, whereby the stable fixation of the first half and the second half of the fixation pair is further secured.

However, as will be well known to the skilled person, the ostomy receiving bag is preferably provided with a cover of a sheet material covering one or both walls. This is to limit the view into the receiving bag.

In one embodiment, a cover sheet at the same wall as the fixation pair is provided with a cut defining a part of the cover which only covers a part of the corresponding wall and is only secured to the wall along the part of the rim being superimposed on the sealed rim of the front and rear walls.

One embodiment of the invention, in which the cut cover sheet only covers the corresponding surface partly, offers an option of folding the bag and putting the folded part under the cover sheet. This folding reduces the size of the bag and keeps the folded end discreetly hidden under the cover sheet and thus ensures discretion. Furthermore, it allows for an easy enlargement of the active volume of the bag simply by withdrawing the end of the bag from under the cover sheet, should a larger collecting volume suddenly be needed in situations where there is difficult or no access to a rest room.

When the cover sheet of the front wall is cut along a line perpendicular to the longest dimension of the front wall the end of the bag is easy to insert and withdraw from behind the cover sheet. Thus, one embodiment relates to an ostomy receiving wherein a cover sheet of the same wall as the fixation pair is cut along a line perpendicular to the longest dimension of the front wall.

It is preferred that the cover sheet of the front wall superimposing the top end of the front wall forms a pocket which will not give rise to folding of the top part of the cover sheet. Consequently, one embodiment of the invention relates to an ostomy receiving bag, wherein a cover sheet of the same wall as the fixation pair superimposes the top end of said wall and forms a pocket.

It has been found suitable when the length of the cover sheet of the front wall is from 25 to 100% of the longest dimension of the front wall which still allows for a considerable temporary reduction of the volume of the bag and reduces the use of raw materials. Thus, it is foreseen that the cover sheet may be in the form of a band covering a part of the front wall.

It is preferred that the cut of the cover sheet of the front wall is placed at a length of from 50 to 75% of the longest dimension of the front wall. In an another embodiment of the invention, the cover sheet being cut covers all of the surface of the corresponding wall and is secured to the wall along the part of the rim being superimposed on the sealed rim of the front and rear walls leaving a slit defining two pockets each covering an end part of the bag.

Thus, in the volume reduced configuration, the one embodiment of the invention relates to an ostomy receiving bag wherein the bottom end of the receiving bag is folded back and stretches under the cover sheet of the same wall as the fixation pair.

In one embodiment of the invention, the wall with the fixation pair is the front wall. This is preferred so the user can unfold outwards (away from the user) in an easy way. However, another embodiment of the invention, the wall with the fixation pair is the rear wall. Hereby is obtained that the folding will not get in touch with the user's clothes. Likewise, the fixation pair, whether attached on un-attached will not get into the user's cloth. Not only does it avoid sticking to the clothes, but it alleviate the tendency of clothes to grap the bottom end of the receiving bag in volume reduced configuration and tear it from the fixation pair, thereby unintentionally unfolding the receiving bag.

It is preferred that the cover sheet is of a porous material as such material may reduce noise from the bag and improve the "breathing" of the skin covered by the bag. Suitable porous materials for use as cover for the purpose of the present invention are woven or non-woven sheet materials which are moisture resistant and may be united with materials conventionally used in the production of ostomy appliances such as non-woven materials of polyethylene, polypropylene or a polyester.

In a further preferred embodiment of the invention the end of the bag opposite the top end is provided with a strip of material extending from the bottom end which will render it easier to grasp and withdraw the folded end of the bag from behind the cover sheet.

Furthermore, it is preferred to secure the strip in a manner that allows an easy removal, so that it e.g. can be torn off, naturally without risk of damaging the welding of the pouch which might lead to leaks, after the expansion or unfolding of the bag in order to reduce any discomfort by the strip stretching from below the pouch in the unfolded state. Thus, it is preferred that the ultimate strength of the strip in the area in which it is secured to the pouch is lower than the tearing strength of the welding of the rim of the pouch.

This may be achieved by securing the strip to the rim of the bag using a welding being weaker than the welding of the rim of the pouch and also weaker than the ultimate strength of the strip itself. Alternatively, the strip may be provided with one or more notches or perforations near the area in which it is secured to the 10 pouch in order to ensure that the ultimate strength in this area is lower than the tearing strength of the welding of the rim of the pouch. The strip may be of any suitable material being compatible with the cover sheet and fulfilling the above requirements.

It is especially preferred that the length of the strip is longer than the distance from the bottom end of the bag in its folded state to the cut off line of the cover sheet as the end of the strip will then protrude from behind the cover sheet and thus be easier to grasp.

The placing of the halves of the fixation pair, and the shape of those pairs, makes it possible to obtain various foldings. In one typical embodiment of the invention, at least one first half of the fixation pair is placed in the top portion of the receiving bag. This will ensure a high degree of volume reduction.

In another embodiment, at least one second half of the fixation pair is placed in the bottom portion of the receiving bag. If combined with the embodiment wherein the first half of the fixation pair is placed in the top portion of the receiving bag, the receiving bag can be folded in to two halves, reducing the volume with 50%, and reducing the length of the bag with similar approximately 50%.

In yet another embodiment, at least one first half of the fixation pair stretches from the top portion of the receiving bag to about the middle of the receiving bag. This will allow the user to wear a receiving bag with adjustable size and volume from about a 50% reduction to 25% reduction.

In another embodiment, at least one second half of the fixation pair stretches from the bottom portion of the receiving bag to about the middle of the receiving bag. These positions of fixation pairs will allow adjustable size from about 50%, when the bottom part is attached to a Z-fold, that is two foldings, resulting in a 67% reduction in volume.

It is presently speculated that the maximum volume reduction with the fewest means and the least hassle to the user is obtained when at least one first half of the fixation pair is placed in the top portion of the receiving bag and at least one second half of the fixation pair is placed about ⅔ down the receiving bag. Folding the bag inbetween the two fixation pairs, and thereafter attaching the fixation pairs to each other will resulting in a gravity mediated folding just "below" the bottom most half of the fixation pair and the bottom of the receiving bag. This Z-fold, will give a 67% reduction in volume and it will only take op 33% of the space of the unfolded receiving bag.

As will be evident the skilled person, combination of the above mentioned placings of the halves of the fixation pairs can be done. For example, multiple sets of fixation pairs are placed along the length of the receiving bag allowing multiple foldings, and providing the user with a feeling of rolling the receiving bag, and a various degrees of foldings can be obtained to suit the user's needs.

Of course, in the simple preferred version one set of fixation pairs are placed on the receiving bag.

In a preferred embodiment the ostomy receiving bag comprises one fixation pair, at least one first half of the fixation pair is placed in the top portion of the receiving bag, and at least one second half of the fixation pair is placed in the bottom portion of the receiving bag, the wall with the fixation pair is the front wall, the ostomy receiving bag is an open bag, and the fixation pair is velcro.

FIGURES

FIG. 1
This figure shows the unfolded embodiment of an open bag 100. Here one piece of a fixation pair (half of a fixation pair) is placed marked with the letter A, and the second piece of the fixation pair (second half of fixation pair) is placed with the letter B. When this open bag 100 is closed, during use, the second half of the fixation pair B, is on the same side as the first half A, here on the front wall 2.

Figure 2:
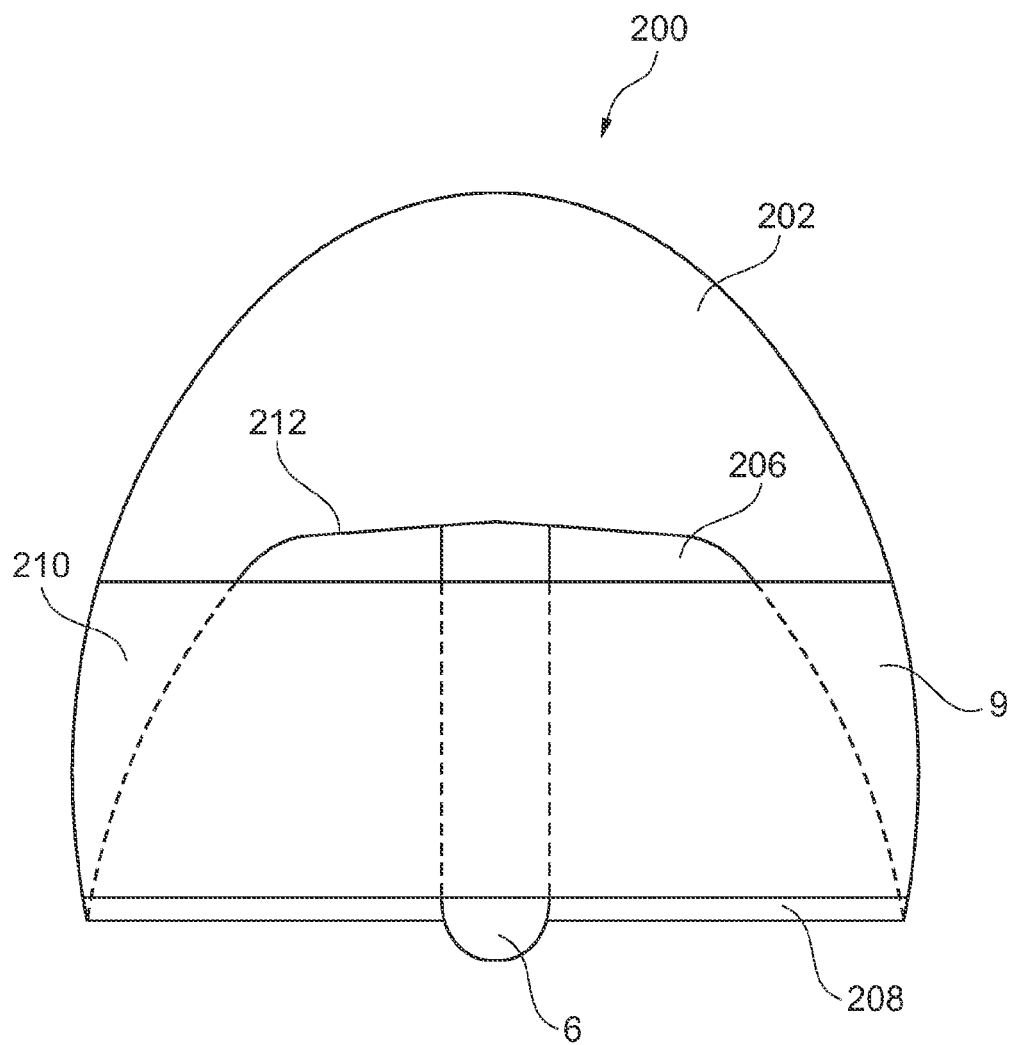

FIG. 2
This figure shows a further embodiment of an ostomy receiving bag 200 according to the invention. Here, the cover sheet 210 of the front wall (202) is cut off at a length of from 25 to 80% of the longest dimension of the front wall 202 and is in the form of a band (9) covering a part of the front wall 202. The bottom end (212) being folded back and stretching under the cover sheet (210) of the front wall (202) and the end of the strip (6) of a sheet material are visible above 206 and below 208 the band 9 formed by the cover sheet 210.

Figure 3:
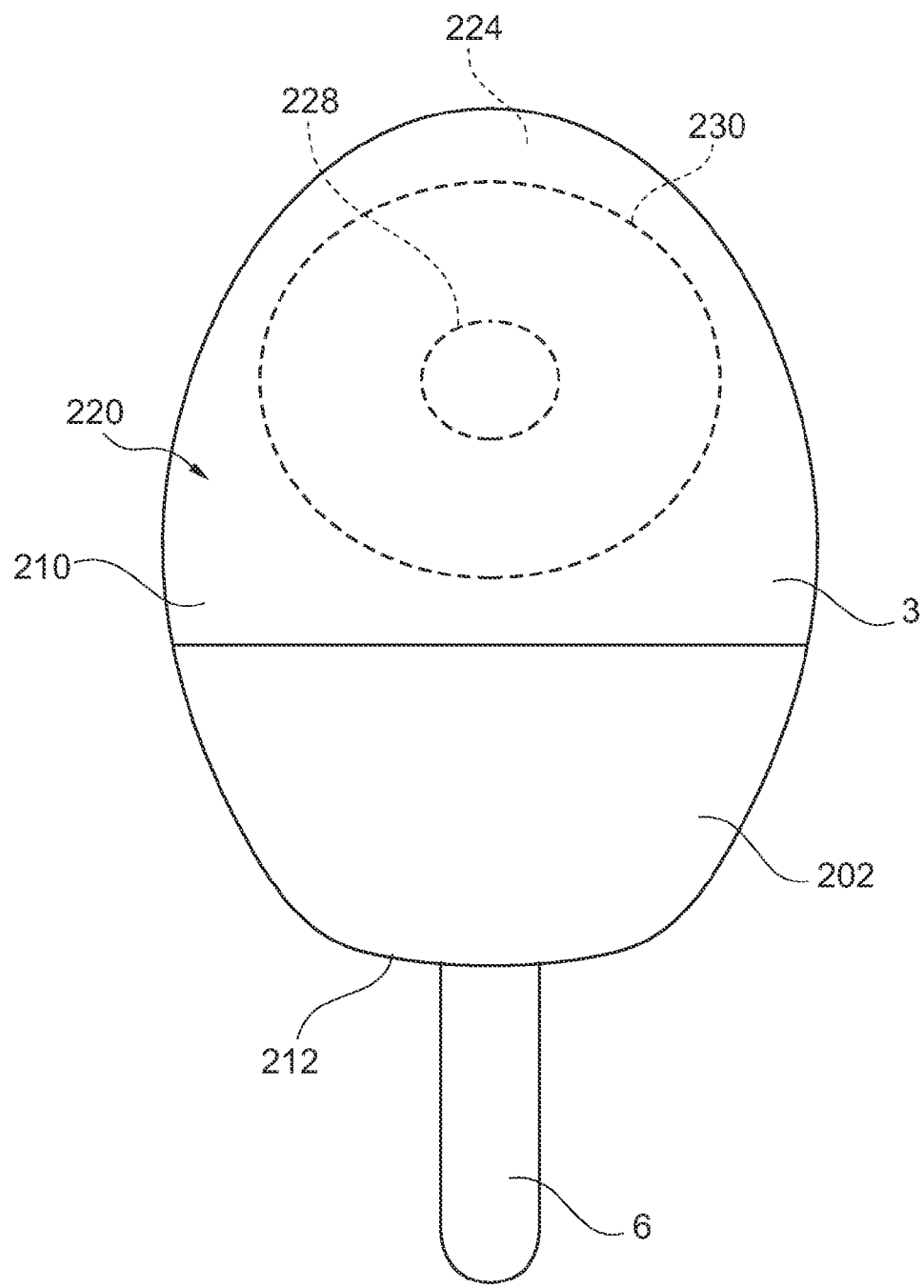

FIG. 3
This figure shows the embodiment of FIG. 2 in an nfolded state, seen from the surface facing away from the user (front wall 202). The figure shows the front wall (202), the cover sheet (210), a top end portion 220 of the rear wall 224 is provided with an inlet 228 and the strip (6) extending from the bottom end 212 and indicating an adhesive wafer 230 situated on the rear wall 224.

The invention claimed is:
1. An ostomy receiving bag comprising a front wall sealed to a rear wall along a sealed rim and having a top end and a bottom end,
the top end of the rear wall is provided with an inlet and the bottom end provides an outlet tail extending away from the front and rear walls with a closable outlet at the bottom end;
a cover sheet separate from the outlet tail and secured to the sealed rim of one of the front and rear walls, the cover sheet including a cut that at least one of a top edge and an opposing bottom edge of the cover sheet has a central portion that is not attached to one of the front and rear walls; and
one of a first half of a fixation pair is placed on a top end portion of the receiving bag, and a second half of the fixation pair is placed on a bottom end portion of the receiving bag;
wherein attachment of the second half of the fixation pair to the first half of the fixation pair locates the outlet tail on the top end portion of the receiving bag between the cover sheet and one of the front and rear walls to reduce a collection volume of the ostomy receiving bag and to cover a majority of the outlet tail from view;
further wherein separation of the second half of the fixation pair from the first half of the fixation pair allows expan- sion of the collection volume of the ostomy receiving bag for use with the closable outlet closed.

2. The ostomy receiving bag according to claim 1, wherein the outlet tail is movable from between the central portion of the cover sheet and one of the front and rear walls to open the receiving bag and thereby increase a volume of the receiving bag.

3. The ostomy receiving bag according to claim 1, wherein the first half of the fixation pair is a hook that is attachable to a hook of the second half of the fixation pair to provide a hook-hook fixation pair.

4. The ostomy receiving bag according to claim 1, wherein the first half of the fixation pair is a hook that is attachable to a loop of the second half of the fixation pair to provide a hook-loop fixation pair.

5. The ostomy receiving bag according to claim 1, wherein the fixation pair is non-tacky adhesive surfaces.

6. The ostomy receiving bag according to claim 1, wherein the fixation pair is one of a press stud fastener and a snap together fastener.

7. The ostomy receiving bag according to claim 1, wherein the fixation pair is glue.

8. The ostomy receiving bag according to claim 1, wherein the fixation pair is press sensitive adhesive (PSA).

9. The ostomy receiving bag according to claim 1, wherein the fixation pair is tape.

10. The ostomy receiving bag according to claim 1, wherein the fixation pair is a button combination.

11. The ostomy receiving bag according to claim 1, wherein the fixation pair is clips.

12. The ostomy receiving bag according to claim 1, wherein the cover sheet is secured to the sealed rim of the front wall and the fixation pair is placed on the front wall.

13. The ostomy receiving bag according to claim 12, wherein the bottom end of the central portion of the cover sheet is not attached to the front wall, the cover sheet superimposed on the top end of the front wall to form a pocket.

14. The ostomy receiving bag according to claim 12, wherein the cover sheet has a length from 25% to 100% of the longest dimension of the front wall.

15. The ostomy receiving bag according to claim 14, wherein the cover sheet has a length from 50% to 75% of the longest dimension of the front wall.

16. The ostomy receiving bag according to claim 1, wherein the cover sheet is a porous material.

17. The ostomy receiving bag according to claim 1, wherein the bottom end is provided with a strip of material extending from the bottom end.

18. The ostomy receiving bag according to claim 17, wherein a strength of the strip at a location of secural to the pouch is lower than a tear strength of a welded rim of the pouch.

19. The ostomy receiving bag according to claim 1, wherein the first half of the fixation pair stretches from the top end portion of the receiving bag to about a middle of the receiving bag.

20. The ostomy receiving bag according to claim 1, wherein the second half of the fixation pair stretches from the bottom end portion of the receiving bag to about a middle of the receiving bag.

\* \* \* \* \*